US00PP23361P2

(12) United States Plant Patent
Warren

(10) Patent No.: US PP23,361 P2
(45) Date of Patent: Jan. 29, 2013

(54) SUGAR MAPLE TREE NAMED 'JFS-CADDO2'

(50) Latin Name: *Acer saccharum*
Varietal Denomination: JFS-Caddo2

(75) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 122 days.

(21) Appl. No.: 12/928,219

(22) Filed: Dec. 6, 2010

(51) Int. Cl.
*A01H 5/00* (2006.01)

(52) U.S. Cl. ..... Plt./224

(58) Field of Classification Search ..... Plt./224
See application file for complete search history.

*Primary Examiner* — Kent L Bell

(74) *Attorney, Agent, or Firm* — Klarquist Sparkman, LLP

(57) ABSTRACT

A variety of sugar maple which combines intense bright red fall color, an upright oval to slightly pyramidal canopy shape, and foliage that is dark green, moderately resistant to powdery mildew, and very resistant to heat.

9 Drawing Sheets

Latin name of the genus and species of the plant claimed: *Acer saccharum.*

Variety denomination: 'JFS-Caddo2'.

BACKGROUND OF THE INVENTION

Sugar maple, *Acer saccharum*, is native to a wide area of North America, generally from eastern Kansas to southern Ontario and from northern Georgia to Newfoundland. A genetically isolated population of sugar maple exists in the Caddo Mountains of Oklahoma, separated from the rest of the sugar maple range. Because the Caddo Mountain population lives beyond the extreme southwest edge of the main sugar maple range, I believed that it might produce seedling trees with increased tolerance to heat and drought. In the early 1990's, I became interested in beginning a selection program for an improved sugar maple from this source.

In the fall of 1994, I obtained seed of sugar maples collected from the Caddo Mountains. I directed planting of these seeds in seedbeds in a nursery in Boring, Oreg. In the spring of 1995, these seeds germinated and grew into healthy small seedlings which resulted in approximately 100 small trees after two years of growth. During the first months of 1997, I harvested these trees. I saved the thirty largest, most vigorous plants and I destroyed the rest. These thirty trees were placed into cold storage then planted out into a nursery row in May of 1997. In the fall of 1999, I evaluated these trees for fall color and growth rate and marked the best twelve trees. In the spring of 2000, I transplanted these best twelve trees into another nursery location in Boring, Oreg., and I destroyed the remaining eighteen trees. Over the next two years, I regularly evaluated these trees for foliage quality, disease resistance, growth rate, branch structure, and fall color. In February 2002, I selected the best five and planted them out on wide spacing in the same nursery and I destroyed the other seven trees.

Over the next several years, I regularly evaluated these five trees and recorded notes on their performance. My attention was first drawn to the original tree of the 'JFS-Caddo2' variety because it had brightest red fall color and also possessed good branch structure, form, and density. Each year, from 2002 through 2008, I propagated small test plots of about ten trees per year of my new variety by T-budding onto *Acer saccharum* seedling rootstock in nursery rows in both Canby, Oreg. and Boring, Oreg. These trees of the 'JFS-Caddo2' variety were evaluated regularly and compared to other varieties of *Acer saccharum*, including several from the Caddo Mountain seed source. In each case, I grew the test trees of the 'JFS-Caddo2' variety for two or three years in the nursery. Trees of the 'JFS-Caddo2' variety propagated in the years 2005 through 2008 have been retained in the nursery in Canby and Boring, Oreg. to build up propagation stock. The original tree of my new variety has also been maintained. All trees of the 'JFS-Caddo2' variety propagated from 2002 through 2004 were destroyed at the conclusion of testing. This asexual propagation by budding on *Acer saccharum* rootstock in Canby and Boring, Oreg. has shown that the characteristics of my new 'JFS-Caddo2' variety of tree are firmly fixed in successive generations. Testing, evaluation, and comparison of 'JFS-Caddo2' with seedlings of the species, including seedlings of the Caddo Mountain seed source and other commercial cultivars of *Acer saccharum* has convinced me that my new variety of tree has desirable growth and appearance characteristics for landscape use.

SUMMARY

This new cultivar possesses a unique combination of characteristics in that it combines early and intense bright red fall color with an upright oval to slightly pyramidal canopy shape and dark green, heat resistant foliage that is moderately resistant to powdery mildew.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
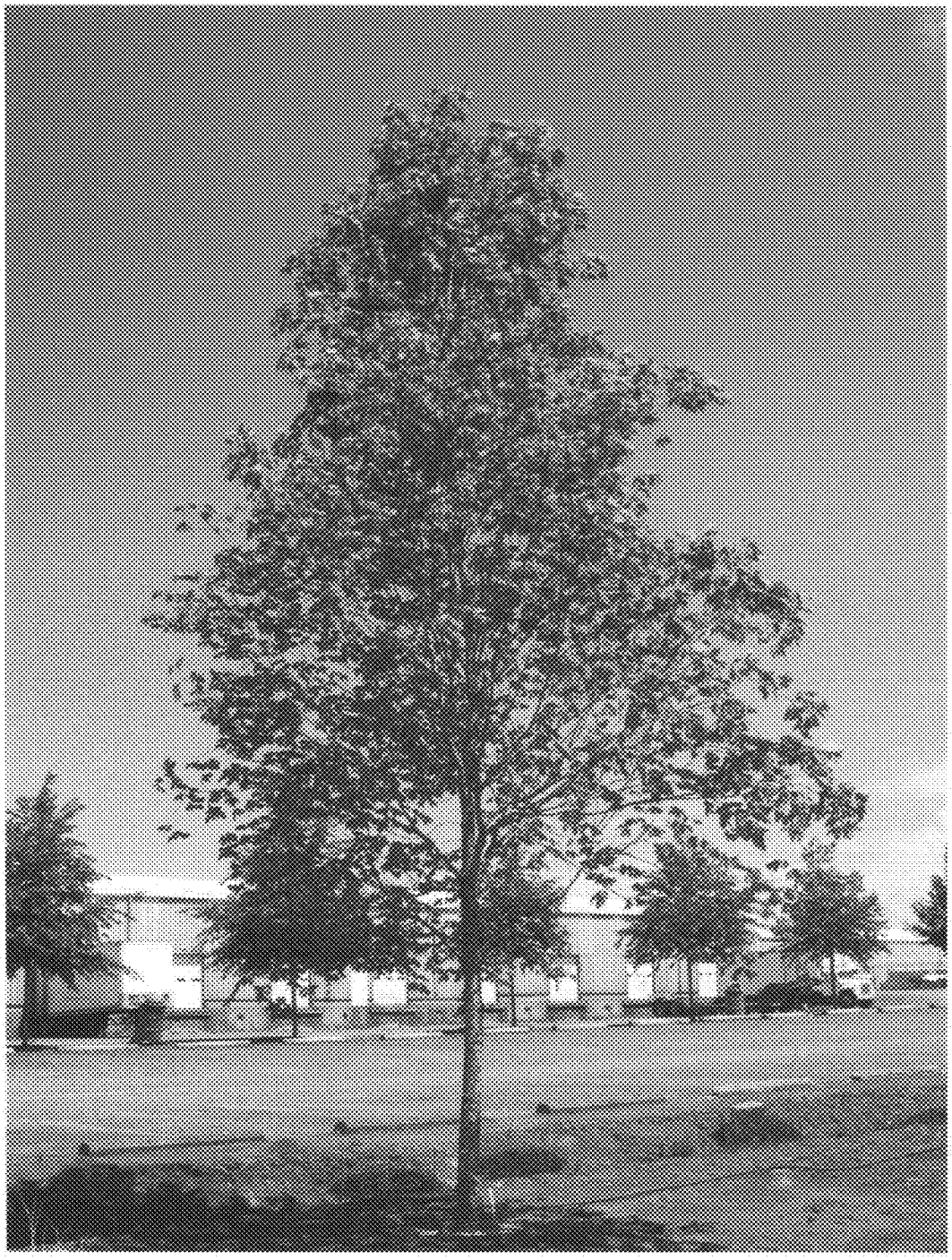
FIG. 1: Shows the original tree of my new variety in summer foliage at age fifteen years, after being transplanted to a final landscape location at the nursery in Boring, Oreg.
Figure 2:
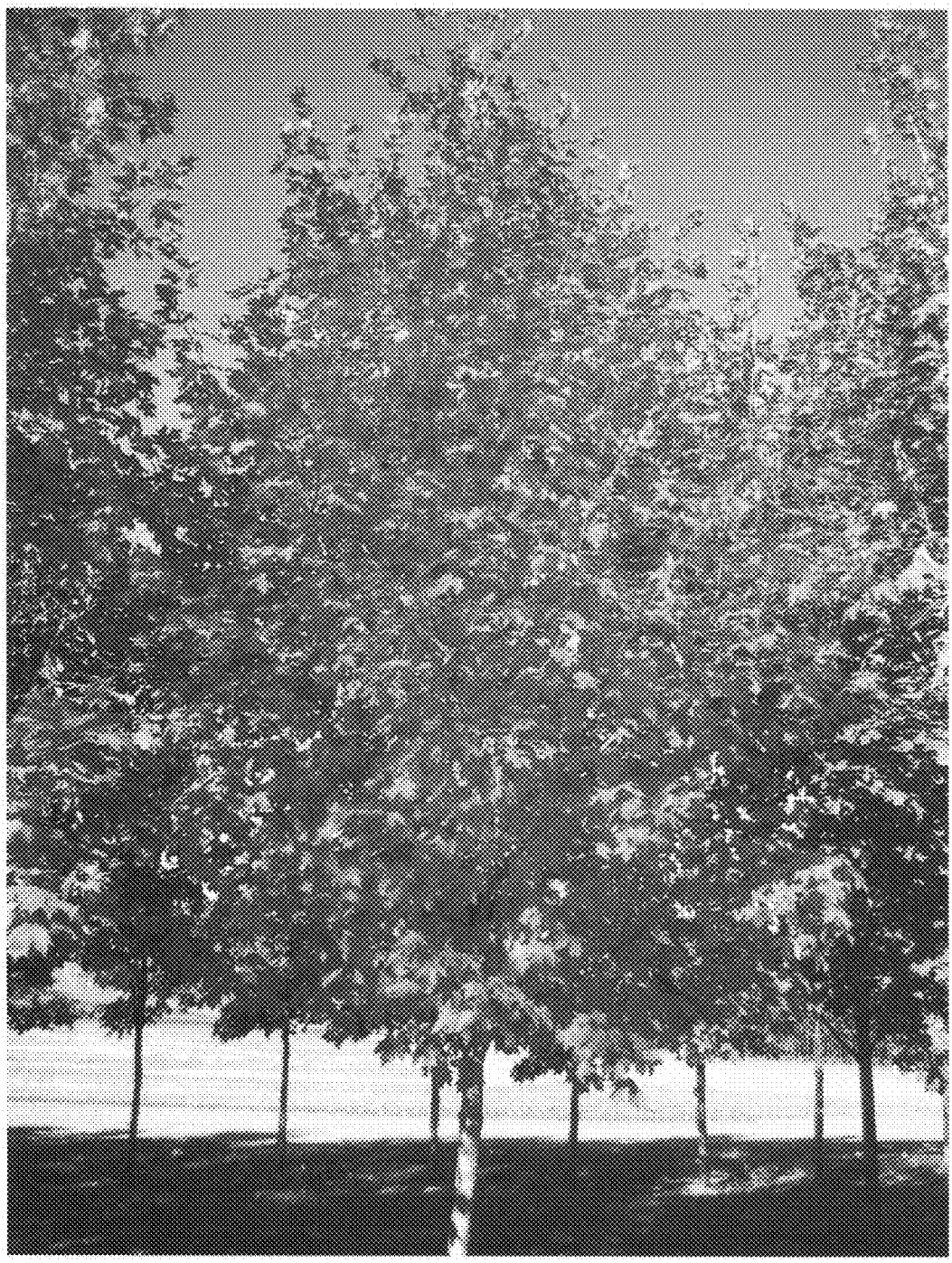
FIG. 2: Shows the original tree at about age twelve years, illustrating its bright fall color in the test block where it was compared to other seedling selections.
Figure 3:
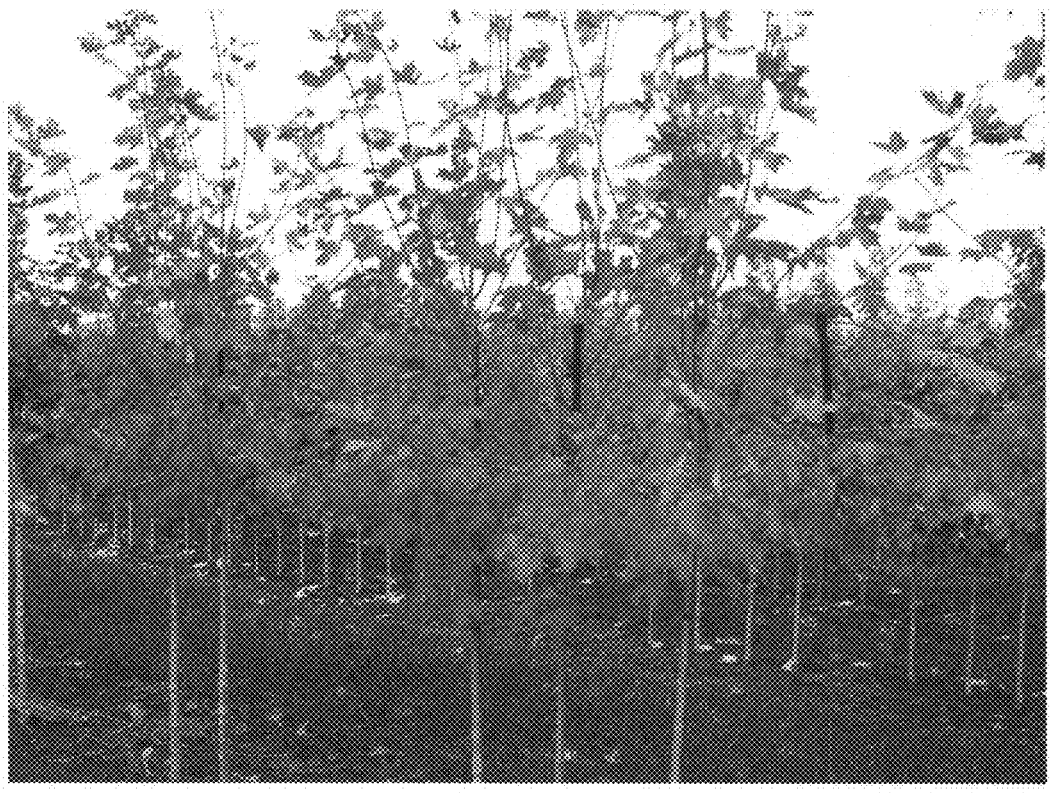
FIG. 3: Shows a plot of two year old trees of my new variety in a nursery row, illustrating that fall color develops at an early chronological age, contrasting with the green foliage of other two year old sugar maples in the background.
Figure 4:
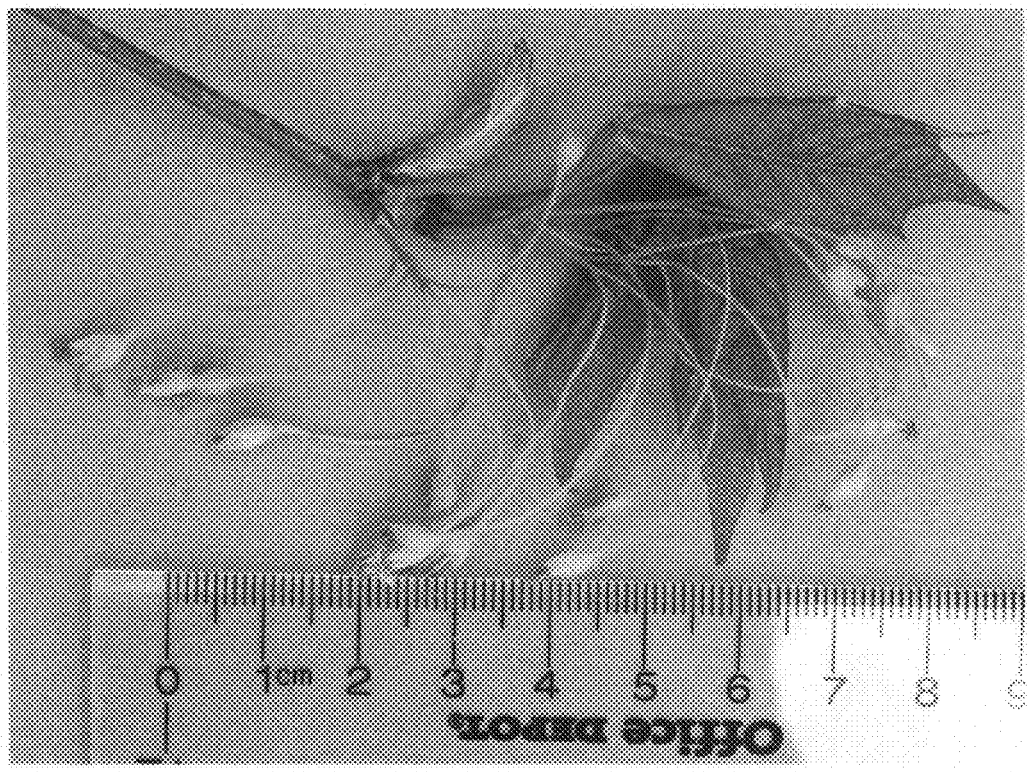
FIG. 4: Shows a cluster of flowers and emerging spring foliage from a tree of my new variety, with staminate flowers on the left and center and three pistillate flowers on the far right.
Figure 5:
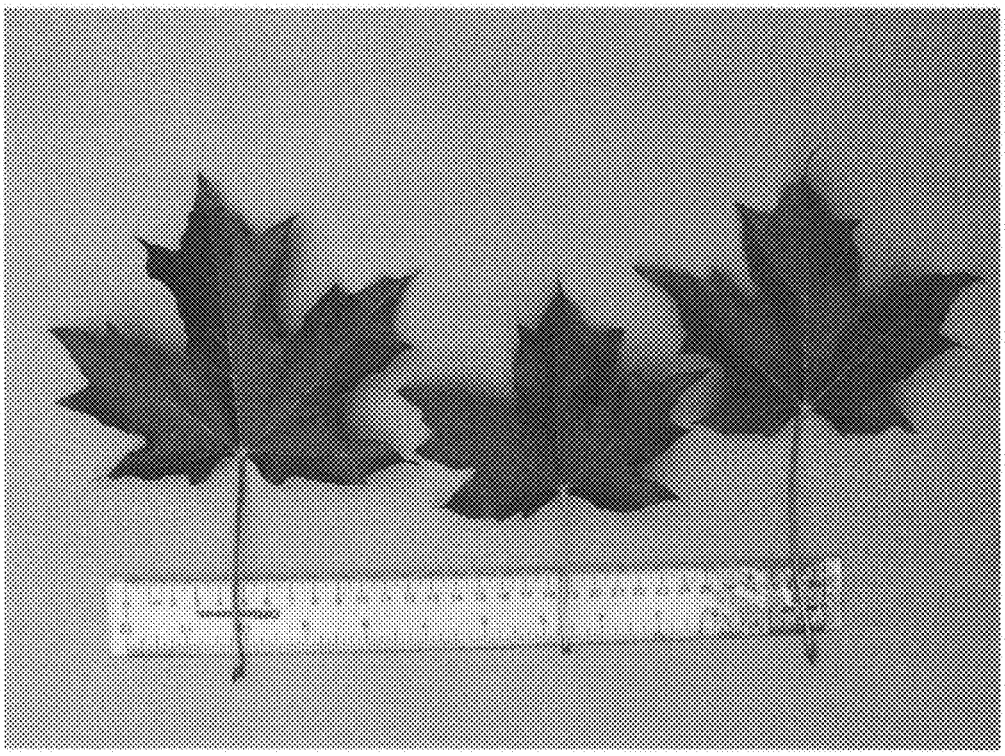
FIG. 5: Shows the upper surface of summer leaves from a tree of my new variety, illustrating the summer leaf color and the pebbly to slightly rugose leaf texture, as well as the reddish petiole on sun exposed leaves, and the greenish petiole on the center leaf, which was growing in the shade.
Figure 6:
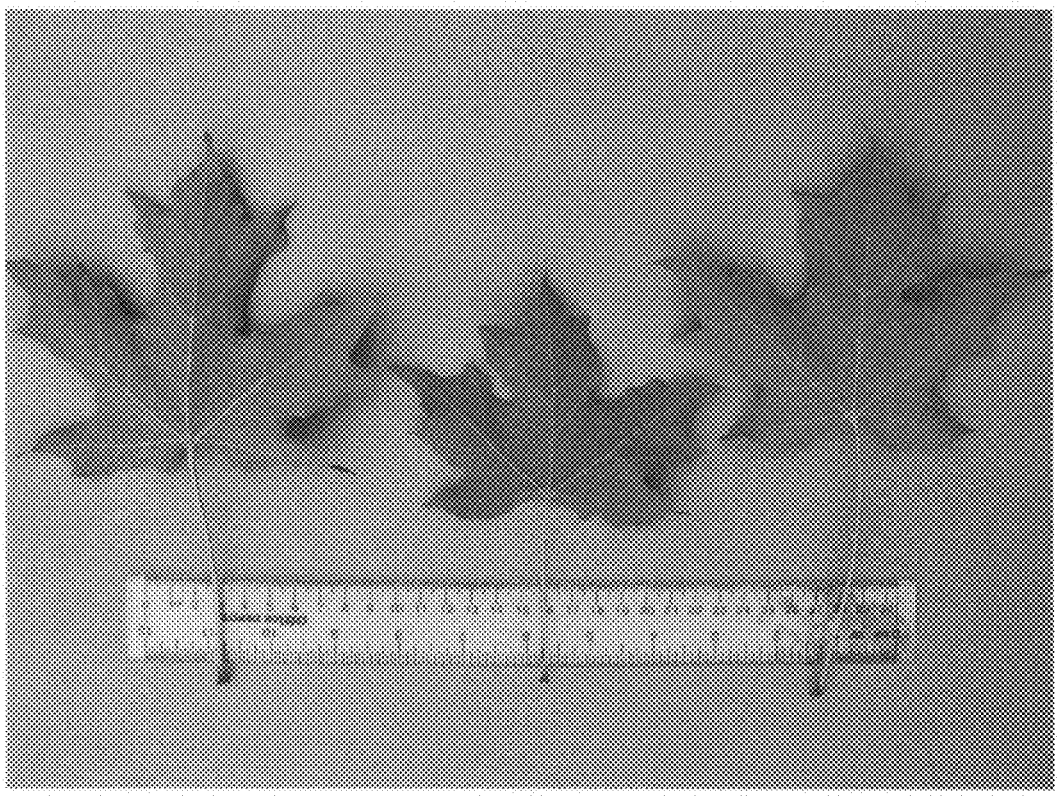
FIG. 6: Shows the lower surface of the same leaves in FIG. 5 and illustrating the greenish coloration of the lower, shaded surface of the petiole.
Figure 7:
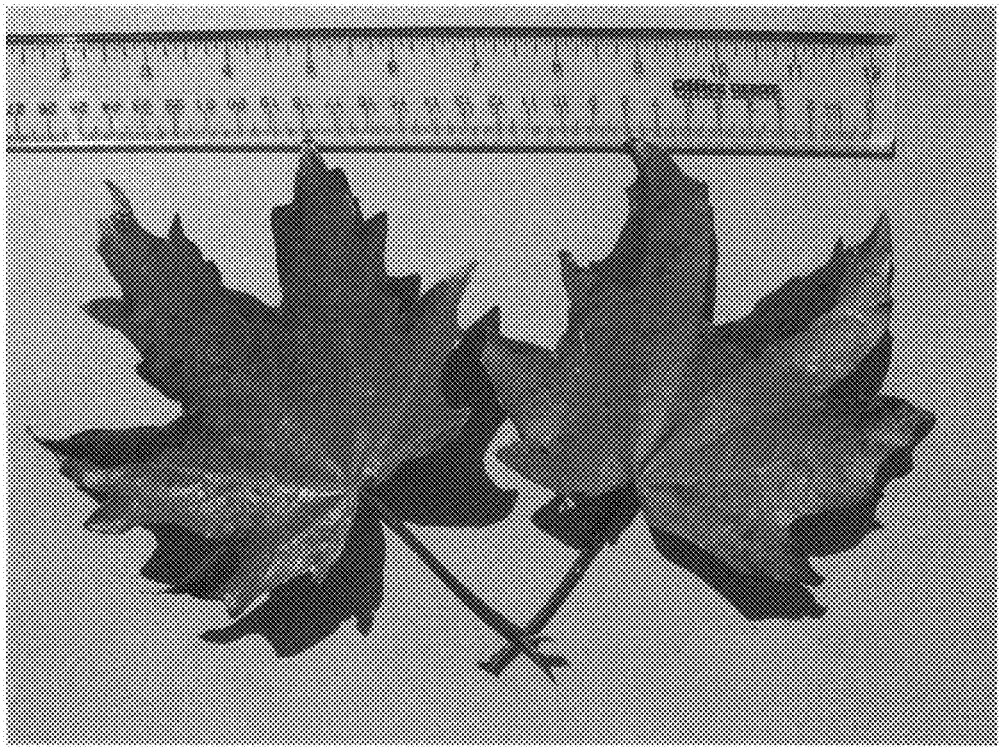
FIG. 7: Shows the upper surface of leaves of my new variety in fall color.
Figure 8:
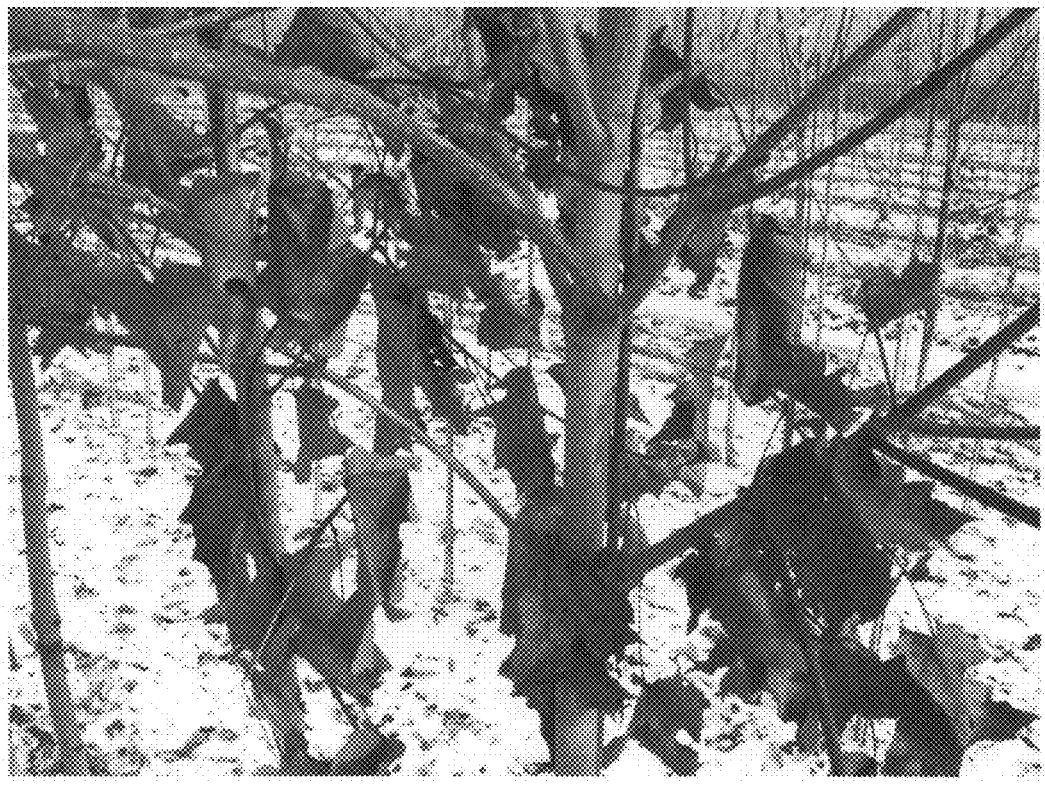
FIG. 8: Shows the marcescent nature of the foliage of my new variety in mid-November.
Figure 9:
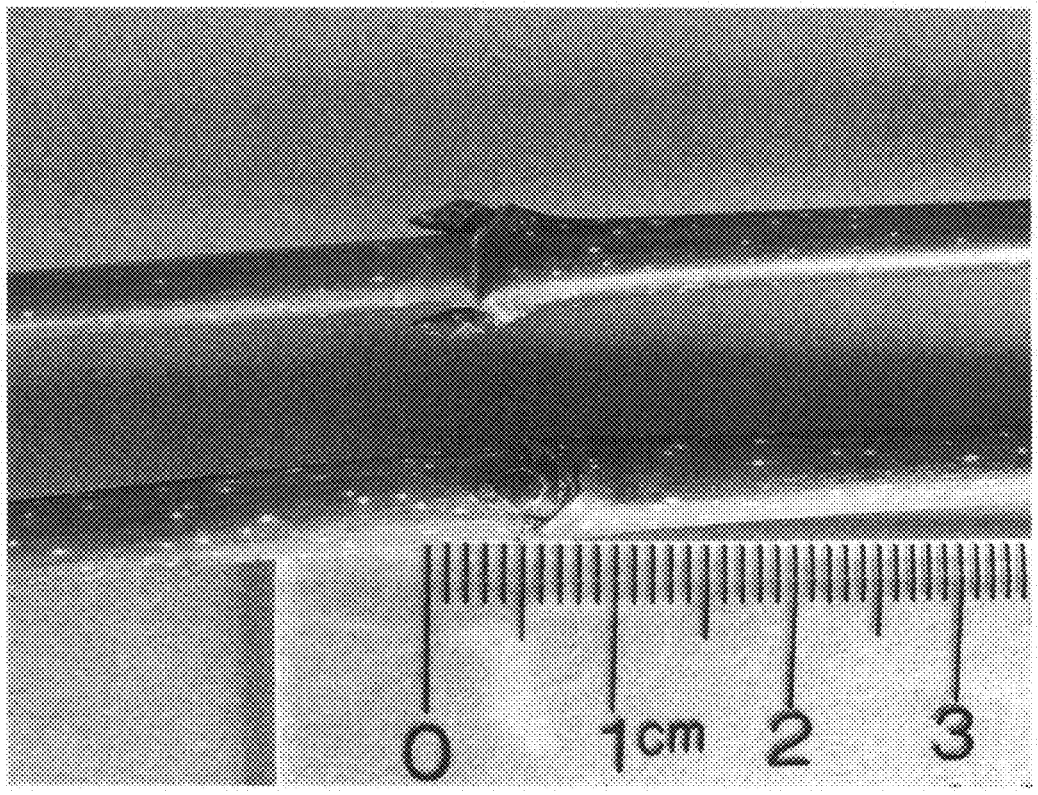
FIG. 9: Shows winter buds from a tree of my new variety, illustrating the typical size, shape, and bud scales.

The following detailed description of the 'JFS-Caddo2' variety is based on observations of the original tree and one, two, and three year old progeny. The observed progeny were trees that were growing in Boring, Oreg. and Canby, Oreg.

The following is a detailed description of my new sugar maple tree, with color descriptions using terminology in accordance with The Royal Horticultural Society (London) Colour Chart© 1986, except where ordinary dictionary significance of color is indicated.

Scientific name: *Acer saccharum* 'JFS-Caddo2'.

Parentage:

*Seed parent*.—An unknown plant of *Acer saccharum*.

*Pollen parent*.—An unknown plant of *Acer saccharum*.

Tree:

*Overall shape*.—Upright oval to slightly pyramidal.

*Height*.—8.1 meters at fifteen years of age.

*Width*.—5.2 meters at fifteen years of age.

*Caliper*.—14.3 cm at 10 cm height above the ground level, 11.9 cm at 1 meter height above the ground level, at fifteen years of age.

*Trunk*.—Straight, strongly upright, single stem with a very gradual taper.

*Trunk bark texture*.—Very slightly and shallowly fissured.

*Trunk bark color*.—Immature bark color: Greyed-Orange 165C. Mature bark color: Greyed-Green 197B to Greyed-Green 197D. Lenticels: Not visible on trunk.

*Primary branches*.—Broadly upsweeping with typical crotch angles that are generally about 30° to 60°. Branch length is proportional to the overall size of the tree, with the longest branches typically measuring approximately 45% of the height of the tree. At 15 years of age, the longest branches on the original tree were 3.6 meters.

*Branch color*.—Young branches are Greyed-Orange 165B to 166A to Grey-Brown 199A during the first winter, smooth and slightly lustrous, then become Greyed-Orange 165C to Grey-Brown 199C, rough textured, at 1 cm to 2 cm diameter.

*Branch lenticels*.—Orange-White 159A, oval to oblong, 1 mm to 2 mm long by 0.5 to 1 mm wide. On new growth branches, lenticel density averages nine per square centimeter when the branch is 5 mm in diameter. On two year old branches, lenticel density averages five per square centimeter when the branch is 10 mm in diameter.

*Dormant buds*.—Narrowly conical with a sharply acute tip and imbricate scales. Greyed-Orange 165A to Brown 200B. Typically 3 mm to 6 mm long by 2 mm to 3 mm wide.

*Bud break*.—Bud break averages April 13 under Boring, Oreg. conditions. Bud break is about five days later than the average for the species.

*Internodes*.—11.2 cm average length on 1 yr tree at 1 meter height. 9.4 cm average length on branches of two year old trees.

*Hardiness*.—Has tolerated field temperatures to 10 degrees F. without damage in Boring, Oreg. This is the minimum temperature this location experienced during the life of the original tree. I lab tested twigs of my new variety to −30 degrees F. on Feb. 1, 2005 without damage. It is believed to have Zone 4 cold hardiness similar to other plants of this species and better than most plants from the Caddo Mountain seed source known to me.

*Disease resistance*.—Moderately resistant to powdery mildew, an improvement over typical seedlings of the species. Much more resistant to powdery mildew than typical seedlings of the Caddo Mountain seed source. Otherwise, disease susceptibility is typical of the species.

Leaves: Except as otherwise noted, observations are from twenty vigorous growth leaves.

*Arrangement*.—Opposite.

*Type*.—Simple.

*Texture*.—Slightly pebbly and very slightly rugose on the upper surface. Smooth except netted by protruding leaf veins on the lower surface.

*Sheen*.—Slightly satiny on the upper surface. Dull on the lower surface.

*Length*.—9 to 16 cm.

*Width*.—11 to 19 cm.

*Petioles*.—6 cm to 12 cm long×2 mm in diameter. Color on the upper surface where exposed to sunlight is Greyed-Purple 184A. Where petiole is in shade, color of upper surface will vary to Yellow-Green 145A. Lower surface of petiole is Yellow-Green 145A.

*Overall shape*.—Palmate with five main lobes, deepest sinuses extend about half way to the center vein, lobe tips are acuminate.

*Margin*.—Smooth, with occasional acuminate minor lobe tips. Lobe lengths are proportional to the size of the individual leaf. The following are averages of the typical length of lobes in a group of observed leaves as a percentage of the overall length from the lobe tip to petiole attachment and in comparison to width of the overall leaf blade: Top middle lobe — length is 50% of lobe tip to petiole measurement and 40% of leaf blade width. Each side lobe — length is 6-0% of lobe tip to petiole measurement and 35% of leaf blade width. Each basal lobe — length is 33% of lobe tip to petiole measurement and 126% of leaf blade width.

*Tip*.—Acuminate.

*Base*.—Cordate.

*Stipules*.—None.

*Spring leaf color*.—First emerging leaves are Red 178D to Red 179A on the upper surface and Yellow-Green 146C to Yellow-Green 146D with a tint of Red 178C on the lower surface.

*Summer leaf color*.—Upper leaf surface: Green 139A. Lower leaf surface: Green 138A to Green 138B. Vein: Green 145C.

*Fall leaf color*.—Fall Leaf Color: Red 45B to Red 46A on upper surface and Red 46C to Red 47C on lower surface at peak. After peak fall color, leaves gradually change to a generally brownish (dictionary color), ranging from Greyed-Orange 177B to Greyed-Orange 177C on upper surface and Greyed-Orange 177C to Greyed-Orange 177D on lower surface. A portion of the leaves defoliate quickly after losing their red fall color, but most defoliate gradually after turning brown (dictionary color), over a period of several weeks.

*Timing of fall leaf color*.—Average dates for original tree in Boring, Oreg.: Onset: October 2. Peak: October 15. Latest extent of red fall color: November 8. Fall color begins and peaks about a week earlier than is typical for the species.

*Defoliation*.—After peak fall color, the tree gradually loses the brightness of its fall color as leaves take on a Greyed-Orange color, as described above. The tree is moderately marcescent. Defoliation begins with the onset of the Greyed-Orange color but occurs over a prolonged period. The tree is typically 50% defoliated on November 15, 75% defoliated by December 20, and 100% defoliated by January 12.

*Pubescence*.—Glabrous on the top surface. Glabrous on the lower surface, except slightly tomentose in the axils of the veins.

*Persistence*.—The tree is deciduous, but is marcescent for a period of time in November and December.

*Heat resistance*.—Sugar maple leaves typically develop "leaf tatter" in intense sunlight, low humidity, and high heat. Leaf tatter is a horticultural term used for the development of numerous small holes in leaves in response to these hot summer conditions. 'JFS-Caddo2' foliage is highly resistant to high heat, low humidity, and intense sunlight, exhibited by developing very little or no leaf tatter under these conditions when observed in Boring, Oreg.

Flowers: Monoecious. Flowers emerge as the foliage unfolds in mid-April. Peak flowering April 15 to April 20 in Boring, Oreg. Flowers held in pendulous corymbs of 7 to 10 flowers, with male and female flowers in the same corymb. Flowers apetalous, narrowly campanulate, with five sepals, held on slender 2.5 mm to 4.0 mm long lightly pubescent pedicels. Typical sepals are Yellow-Green 151A to Yellow-Green 151B, fused at the base, papery thin, bract-like, 3 mm long, 2 mm wide at the base and tapering to an irregularly rounded to truncated tip with an often frayed margin. Pedicels are typically 0.5 mm to 1.0 mm in diameter, 2 cm to 5 cm in length, Yellow-Green 151A to Yellow-Green 151B, and the light pubescence is Yellow-White 158D. Staminate flowers are typically 6 mm to 8 mm in overall length by 3 mm in diameter, generally with eight exserted stamens. Stamens are 4 mm to 6 mm in overall length with filaments that measure 3 mm to 5 mm in length by 0.3 mm in diameter. Filament color is Green-White 157D. Anthers measure 1.5 mm long by 0.6 mm wide, Greyed-Orange 163A to Greyed-Yellow 162A. Pistillate flowers are typically 10 mm to 15 mm in diameter. They have a single pistil with two carpels. The typical style is very short, 1 mm to 2 mm in length, 1 mm in diameter. The stigma is split from the base into two parts that are elongated and exserted, each typically 1 mm wide×5 mm to 7 mm long, Yellow-Green 151B to 151C.

Fruit: No fruit has been observed in my new variety. The original tree and other trees of my new variety have yet to produce seed.

COMPARISON TO THE SPECIES

My new variety has brighter and more intense red fall color than any seedling originated trees of the species that I have observed. My tree's fall color is typically Red 45B to Red 46A at peak, while typical seedling originated trees of the species have fall color from Yellow-Orange 22A to Red 43A at peak coloration. In addition, my new variety has moderately marcescent foliage, a very unusual trait for the species which typically defoliates quickly after developing fall color. My new variety is resistant to high heat conditions and shows little or no leaf tatter under such conditions, while typical seedling originated trees of the species show significant leaf tatter under such conditions.

COMPARISON TO OTHER CULTIVATED VARIETIES

My new variety is most similar to the 'Autumn Splendor' and 'John Pair' cultivars (not patented) of *Acer saccharum*. My variety differs from 'Autumn Splendor' primarily in that its foliage develops a more intense, saturated, and pure color of red, that it has a slightly satiny pebbly leaf surface, and in that it is moderately marcescent. My variety differs from 'John Pair' in that it is much faster growing, forms a more upright oval to slightly pyramidal canopy, has a slightly satiny pebbly leaf surface, and has much better resistance to powdery mildew. Table 1 defines these and other differences.

TABLE 1

| Feature: | 'JFS-Caddo2' | 'Autumn Splendor' | 'John Pair' |
|---|---|---|---|
| Leaf sheen | Slightly satiny | Glossy | Glossy |
| Leaf surface texture | Pebbly, slightly rugose | Nearly smooth | Nearly smooth |
| Fall color, peak | Red 45B to Red 46A | Greyed-Red 182A becoming Orange-Red 32A to Red 43B | Greyed-Red 180B to Red 43A |
| Leaf persistence | Moderately marcescent | Not marcescent | Not marcescent |
| Mature tree shape | Upright oval to slightly pyramidal | Upright oval | Broadly rounded |
| Powdery mildew susceptibility | Moderately resistant | Moderately susceptible | Highly susceptible |
| Cold damage to two year old trees in nursery at 10 degrees F., Boring, OR | No damage | Terminal bud killed | Terminal bud killed |
| Height, one year old tree in nursery, Boring, OR | 2.3 meters | 2.4 meters | 1.6 meters |

I claim:

1. A new and distinct variety of sugar maple tree, substantially as herein shown and described.

* * * * *

UNITED STATES PATENT AND TRADEMARK OFFICE

CERTIFICATE OF CORRECTION

PATENT NO. : PP23,361 P2
APPLICATION NO. : 12/928219
DATED : January 29, 2013
INVENTOR(S) : Keith S. Warren It is certified that error appears in the above-identified patent and that said Letters Patent is hereby corrected as shown below:

In the Specification:

Column 4, line 63, "6-0%" should read -- 60% --

Signed and Sealed this
Sixteenth Day of July, 2013

Teresa Stanek Rea
*Acting Director of the United States Patent and Trademark Office*